United States Patent [19]

Bickelman

[11] Patent Number: 4,976,299

[45] Date of Patent: Dec. 11, 1990

[54] STERILE DISPOSABLE COVER FOR A CYLINDRICAL HANDLE

[76] Inventor: Harry M. Bickelman, 9017 Wooded Glen, Louisville, Ky. 40220

[21] Appl. No.: 371,939

[22] Filed: Jun. 27, 1989

[51] Int. Cl.⁵ .............................................. B65D 65/02
[52] U.S. Cl. .................................... 150/155; 206/223; 362/804; 16/114 R; 16/DIG. 24
[58] Field of Search ............... 206/363, 365, 382, 306, 206/223, 438, 223; 362/804, 399, 400, 285; 16/116 R, 114 A, 114 R, DIG. 24; 150/155

[56] References Cited

U.S. PATENT DOCUMENTS

| | | | |
|---|---|---|---|
| 2,197,326 | 4/1940 | Streyle | 206/427 |
| 3,894,807 | 7/1975 | Betz III | 16/114 R |
| 4,061,226 | 12/1977 | Essen | 206/306 |
| 4,316,237 | 2/1982 | Yamada et al. | 362/804 |
| 4,559,671 | 12/1985 | Andrews et al. | 362/804 |
| 4,605,124 | 8/1986 | Sandel et al. | 206/223 |
| 4,621,735 | 11/1986 | Coon et al. | 206/439 |
| 4,720,910 | 5/1988 | Staebler | 206/365 |
| 4,844,252 | 7/1989 | Barron et al. | 206/223 |

Primary Examiner—David T. Fidei
Attorney, Agent, or Firm—Wood, Herron & Evans

[57] ABSTRACT

A sterile disposable plastic cover for a handle of an operating room fixture such as a cylindrical handle for a light fixture is disclosed. The cover includes a hollow member which is open at one end and includes a hand guard. The open end is partially restricted with a retention member which permits the handle of the operating fixture to extend through the open end of the hollow member and holds it in place. Preferably, the retention member is a disc which includes a pair of intersecting slits which define an opening smaller than the opened end of the hollow member.

6 Claims, 1 Drawing Sheet

STERILE DISPOSABLE COVER FOR A CYLINDRICAL HANDLE

BACKGROUND OF THE INVENTION

In an operating room a sterile environment must be established and maintained. Everything which is in the operating or sterile field must be sterilized. Certain items are sterilized after each use. Also many sterile disposable items are employed in the operating room. These include disposable needles, needle count boxes, operating room clothing and the like. It is frequently more economical to use disposable sterile items as opposed to sterilizing reusable items.

Unfortunately, this is impossible with large expensive items used in the operating room. Fixtures such as carts, light fixtures, faucets with faucet handles and the like cannot be made disposable. Any item which is touched by the surgeon or anyone else who enters the sterile field of an operation must be sterilized.

The handles of operating room light fixtures are removable so that in between each operation they can be removed and sterilized thus maintaining the sterile field. This is particularly disadvantageous. It requires very expensive personnel time and sterilizing equipment. Further, one must purchase many additional handles which are very expensive.

To overcome this problem with, in particular light fixture handles, there is currently marketed a disposable cover for a light handle as is disclosed in Sandel U.S. Pat. No. 4,605,124. The sterile cover disclosed in this patent requires that the handle for a light fixture be replaced with a specially shaped light handle which has a bell shaped portion. The cover in turn mates with the bell shaped portion holding it in place. Adhesive can also be used with this to hold it in place.

This is particularly inefficient and wasteful in that the original handle of a light fixture must be replaced with a handle specifically adapted for the cover.

SUMMARY OF THE INVENTION

The present invention is premised on the realization that a cover for a handle of an operating room fixture can be made which is adapted to fit a variety of different sized and shaped handles eliminating the need to purchase expensive custom handles.

Such a cover includes a generally cylindrical body which is open at only one end and includes a guard at the open end to prevent the surgeon's hand from sliding off the cover. The open end of the hollow member includes a retention member which is adapted to allow the handle to pass the retention member and slide into the interior of the hollow member. The retention member then acts to hold the cover in place over the handle during the operation.

In a preferred embodiment, the retention member is a cylindrical disc which covers the open end of the hollow members and includes two intersecting slits which form a cross-shaped opening. This opening is substantially less than the size of the open end of the hollow member but flexes to permit a handle to pass through.

This cover is particularly suitable for the cylindrical handle of an operating room light fixture which must be touched by a surgeon. It can also be adapted for use in a variety of different handles such as faucet handles, cart handles and the like. Further, due to the flexibility of the retention member one size of cover can be employed for a variety of different sized handles.

The objects and advantages of the present invention will be further appreciated in light of the following detailed description and drawings wherein:

DETAILED DESCRIPTION OF THE INVENTION

Figure 1:
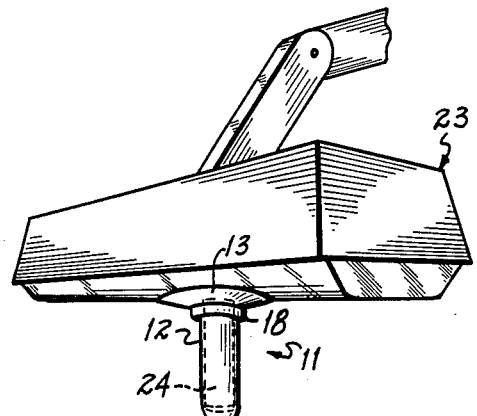
FIG. 1 is a perspective view of an operating room light fixture with a handle cover according to the present invention.
Figure 2:
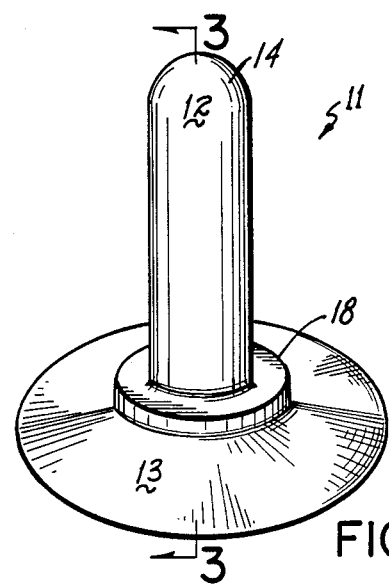
FIG. 2 is a perspective view of a cover for a handle as per the present invention.
Figure 3:
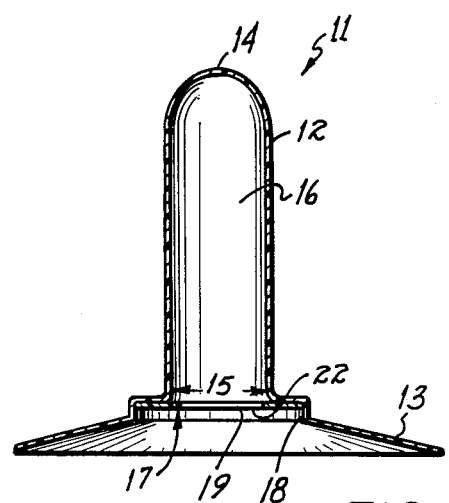
FIG. 3 is a cross-sectional view taken at lines 3—3 of FIG. 2.

As shown more particularly in FIGS. 2 and 3, the present invention is a cover for the handle of a fixture in an operating room. The cover 11 is a disposable sterile plastic cover which is adapted to fit over and be held attached to the handle of a fixture in an operating room. This is shown in place in one embodiment in FIG. 1 where it is attached to the handle of a light fixture. The cover 11 includes a cylindrical hollow member 12 and an annular flange 13. The hollow member 12 includes a closed end 14 and an open end 15 which of course has a defined diameter.

The hollow interior 16 of hollow member 12 is adapted to be at least as large as if not larger than the handle of a fixture in an operating room such as a handle for a light fixture. Cover 11 includes a retention member 17 which partially closes the opening or open end 15 of hollow member 12. This is shown more particularly in FIG. 4.

In this embodiment, the retention member 17 is a circular plastic disc which is adhered within an annular recessed portion 18 in the guard 13. This recessed portion forms an annular ledge in guard 13.

Figure 4:
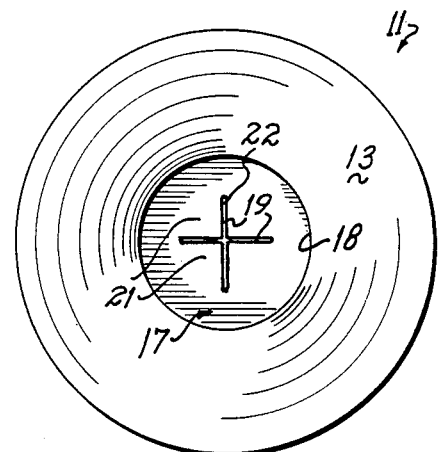
FIG. 4 is a bottom plan view of a cover made according to the present invention.

Retention member 17 includes a plurality of intersecting slits 19 (two are shown in FIG. 4). These slits cut the retention disc 17 into wedges or ears 21 which are flexible and adapted to bend inwardly into the interior 16 of the hollow member 12. The slits also define a restricted opening 22 (cross shaped in FIG. 4) which is of course less than the size of the opening at the open end 15.

As shown in FIG. 1, cover 11 is adapted to cover the handle of a light fixture such as that 23 shown in FIG. 1. Light fixture 23 includes a rod shaped handle shown in dashed lines 24. The rod shaped handle has a size that does not completely fill the interior 16 of hollow member 12. However, it is larger than the restricted opening 22 created by slits 19. Thus, as the cover 11 is forced over handle 24 the wedges 21 bend inwardly and press against the handle 24 which holds the cover in place. Since these members are relatively flexible the handle cover can be easily removed when desired. However, when one grabs the cover 11 pressing against the handle to move the light fixture the cover will remain in place.

This cover 11 is formed from a plastic material and then subsequently sterilized. Preferably, it is vacuum formed from a disc of polyethylene or polypropylene. Guard 13 is about 20 mils thick and retains its shape and position relative to hollow member 12. This enables it to act as a guard and prevent the surgeon's hand from contacting the light fixture. Retention disc 17 is also formed from a piece of polyethylene or polypropylene which is simply adhered into the recess 18.

Figure 5:
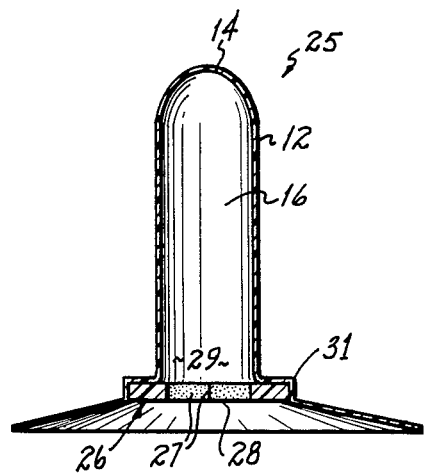
FIG. 5 is a cross-sectional view of an alternate embodiment of the present invention.

Many different alternate forms of the retention member 17 can be used in practicing the present invention. One alternative embodiment 25 is shown in FIG. 5 wherein a flexible urethane foam retention disc 26 is employed which also includes a plurality of slits 27 which divide the retention disc into a plurality of wedges 28 to define an opening 29. This foam piece 26 like the retention ring 17 is heat sealed or glued into the annular recess 31 of alternate embodiment 25.

Other alternate embodiments of the retention member which are not shown would include an elastomeric retention member which has an opening which is smaller than the opening of the open end of the hollow member of the cover. Alternately a plurality of elastomeric bands could be employed to cover the opening.

The cover of the present invention can also be modified by changing the diameter or height of the hollow member 12 as shown in FIGS. 1 and 2 to cover different articles. For example, a shorter wider hollow member could be used to cover the handle of a faucet. A substantially smaller guard could be used to cover a light switch and so on. Even the knobs of a radio in an operating room could be covered with the cover made according to the present invention.

Due to the flexibility provided by the retention member one size of these handles could be useful for a wide variety of different sized and shaped articles. For example, a cover wherein the height of the hollow member is approximately 5¼" and the width is approximately 1 ½ to 1 ¾ inches in diameter provides an excellent cover which is adaptable to fit over most handles for operating room light fixtures. This facilitates distribution of the covers and substantially reduces cost.

One of ordinary skill in the art can make further modifications of the retention member as well as the size and height of the hollow member to facilitate different applications for this disposable sterile plastic cover. However, the present invention should be defined only by the appended claims wherein

I claim:

1. A sterile disposable cover for a handle of an operating room fixture comprising:
   a hollow member having a first closed end and a second opened end having an opening adapted to receive a handle of the operating room fixture;
   a flange extending radially outward from said hollow member;
   a flexible retention member fixed at the juncture of the flange and opened end partially restricting the opening of the hollow member and adapted to engage handles of operating room fixtures of different dimensions.

2. The cover claimed in claim 1 wherein said retention member is a plastic disc having a plurality of intersecting slits.

3. The cover claimed in claim 2 wherein said plastic disc is a flexible foam plastic.

4. The cover claimed in claim 1 wherein said retention member is an elastomeric member having an opening less than the size of said opened end.

5. The cover claimed in claim 1 wherein said cover includes annular recess at said opened end and wherein said retention member is adhered to said annular recess.

6. A sterile disposable cover for the handle of an operating room light fixture comprising:
   a hollow member having a first closed end and second opened end;
   a flange extending radially outward from said hollow member;
   a retention member fixed to said cover and covering the opened end of said hollow portion, said retention member comprising a plastic disc having a plurality of intersecting slits defining an opening, said retention disc including a plurality of flexible wedge-shaped portions adapted to flex inwardly to permit a handle to enter the hollow member and press against said handle to hold said cover to said handle.

* * * * *